(12) United States Patent
Shaw et al.

(10) Patent No.: US 7,670,820 B2
(45) Date of Patent: Mar. 2, 2010

(54) CHITINASE AND USES THEREOF

(75) Inventors: Jei-Fu Shaw, Taipei (TW); Yu-Ting Chen, Shi-Zhi (TW); Lien-Hua Hsu, Sanchong (TW)

(73) Assignee: Academia Sinica, Taipei (TW)

( * ) Notice: Subject to any disclaimer, the term of this patent is extended or adjusted under 35 U.S.C. 154(b) by 3 days.

(21) Appl. No.: 12/013,518

(22) Filed: Jan. 14, 2008

(65) Prior Publication Data

US 2008/0175876 A1    Jul. 24, 2008

Related U.S. Application Data

(60) Provisional application No. 60/880,013, filed on Jan. 12, 2007.

(51) Int. Cl.
*C12N 9/26* (2006.01)
*C12N 9/00* (2006.01)
*C12N 1/20* (2006.01)
*C12N 15/00* (2006.01)
*C07H 21/04* (2006.01)

(52) U.S. Cl. .................... 435/201; 435/183; 435/252.3; 435/320.1; 536/23.2

(58) Field of Classification Search .................. None
See application file for complete search history.

(56) References Cited

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Bhushan, B., "Production and Characterization of a Thermostable Chitinase from a New Alkalophilic *Bacillus* sp. BG-11," *Journal of Applied Microbiology*, 88:800-808 (2000).
Deng et al., "Overexpression of an Endochintase Gene (*ThEn-42*) in *Trichoderma atroviride* for Increased Production of Antifungal Enzymes and Enhanced Antagonist Action Against Pathogenic Fungi," *Appl. Biochem. Biotechnol.* 142:81-94 (2007).
Duo-Chuan et al., "Purification and Partial Characterization of Two Chitinases from the Mycoparasitic Fungus *Talaromyces flavus*," *Mycopathologia*, 159:223-229 (2005).
Kirubakaran, S. Issac and N. Sakthivel, "Cloning and Overexpression of Antifungal Barley Chitinase Gene in *Escherochia coli*," *Protein Expression and Purification* 52:159-166 (2007).
Singh et al., "Heterologous Expression of New Antifungal Chitinase from Wheat," *Protein Expression and Purification*, 56:100-109 (2007).
Ye et al., "A Chitinase with Antifungal Activity from the Mung Bean," *Protein Expression and Purification*, 40:230-236 (2005).

* cited by examiner

*Primary Examiner*—Christian L Fronda
(74) *Attorney, Agent, or Firm*—Occhiuti Rohlicek & Tsao LLP

(57) ABSTRACT

Disclosed herein are novel chitinase polypeptides and nucleic acids encoding the polypeptides. Also disclosed are related vectors, host cells, compositions, and uses.

9 Claims, No Drawings

CHITINASE AND USES THEREOF

RELATED APPLICATIONS

This application claims priority to U.S. Provisional Application No. 60/880,013, filed on Jan. 12, 2007, the contents of which are incorporated herein by reference.

BACKGROUND

Chitinases (EC 3.2.1.14), enzymes catalyzing hydrolysis of chitin, exist in various organisms including viruses, bacteria, fungi, insects, plants, and animals. Chitin, a linear β-1,4-linked homopolymer of N-acetyl-D-glucosamine (GlcNAc) is widely distributed in fungal cell walls, the exoskeleton of arthropods, and the outer shell of crustaceans. Chitinolytic activity is involved in food digestion, morphogenesis, and degradation of cuticle. In higher plants that lack endogenous substrates, chitinases are involved in the defense against pathogens and function as pathogenesis-related (PR) proteins (Collinge et al. 1993, Plant J. 3, 31-40.3). Among various PR-proteins, chitinases and β-glucanases hydrolyze chitin and β-1-3-glucan, which are the major structural components in the cell wall of many phytopathogeneic fungi (Selitrennikoff, 2001, Appl. Environ. Microbiol. 67, 2883-2894). Chitinases, like β-glucanases, contribute to plant defenses due to their ability to degrade fungal pathogens cell wall, and thereby inhibit their growth. In the early stage of pathogenesis, apoplastic chitinases release elicitor molecules that activate the defense mechanisms of plants. Then the synthesis and secretion of apoplastic chitinases occur to enhance the infection signaling, while the vacuolar chitinase degrades the fungal cell wall to inhibit pathogen growth (Collinge et al. 1993, Plant J. 3, 31-40). Chitinases have been used in agriculture to control plant pathogens (Broglie et al., 1989, Plant Cell 1, 599-607.)

Based on similarity in the catalytic domains of glycosyl hydrolases, chitinases have been classified into families 18 and 19 (van Aalten et al., 2001, Proc. Natl. Acad. Sci. USA 98, 8979-8984). Chitinases can also be divided into two categories based on function: exochitinases and endochitinases. Exochitinases specifically hydrolyze the β-1,4-glycoside linkages at the non-reducing end of the chitin chain, whereas endochitinases cleave the internal linkages. Some plant endochitinases have lysozyme activity and hydrolyze the β-1,4-linkages between N-acetylmuramic acid and GlcNAc residues in peptidoglucan (Subroto et al., 1999, J. Mol. Evol. 49, 819-821. Transgenic Res. 15, 337-347).

SUMMARY

The present invention is based, at least in part, on the unexpected discovery of a novel chitinase from papaya fruit.

Shown below are the open reading frame sequence (SEQ ID NO: 1) and the polypeptide sequence (SEQ ID NO: 2) of this novel chitinase.

```
SEQ ID NO: 1:
                                      atgt cgccaaacaa tgccttactc
ctttctcttc ccctccttgt ttccttgctc atttcggcca tgcccagacc agtaacgagc
cagaactgtg gctgtgcgcc caacttatgt tgtagcaggt tcgggttctg tggccagggc
gaggcgtatt gcggcgaggg atgccgggaa ggtccatgca ataagccgtc gcctactcct
ggcggcggca gttcacttgc agagatcgtc actcccgatt tcttcaacgg aataattaat
caagcggctg ccggctgtgc cgggaagagt ttttgctcgc gaggtggctt tctagatgct
gctaattcgt ttcccgaatt tggaaaactt ggttcagtcg atgattctaa gcgtgagatt
gctgcgtttt tcgctcatgt cacccatgaa actggacatt tttgtcacat cgaagaaata
aatggagctt ctcatgacta ttgcgacgag ggaaacacac aataccttg tgcaccaggg
aagaactact tcggccgagg accgattcag ctaacatgga attacaacta cggagcagcc
ggtgatgcct tgaggctcaa cttgttaggc tcgccggaga tggtggcaag agatgctgca
gtttccttca agacagcctt gtggttttgg atgaagaatg tccggccggt gatcaaccaa
gggttcggtg caaccattcg agccatcaac ggtgcaatag agtgcaatgg gggaaatcca
ggaactgttc aggctcgtat tggttattat agagattatt gtgctaaatt tggtgttgct
cctggtgaaa atctcagttg tta SEQ ID NO: 2
Met Ser Pro Asn Asn Ala Leu Leu Leu Ser Leu Pro Leu Leu Val Ser
1               5                   10                  15

Leu Leu Ile Ser Ala Met Pro Arg Pro Val Thr Ser Gln Asn Cys Gly
                20                  25                  30

Cys Ala Pro Asn Leu Cys Cys Ser Arg Phe Gly Phe Cys Gly Gln Gly
                35                  40                  45

Glu Ala Tyr Cys Gly Glu Gly Cys Arg Glu Gly Pro Cys Asn Lys Pro
                50                  55                  60
```

```
Ser Pro Thr Pro Gly Gly Gly Ser Ser Leu Ala Glu Ile Val Thr Pro
 65              70              75                  80

Asp Phe Phe Asn Gly Ile Ile Asn Gln Ala Ala Gly Cys Ala Gly
                 85              90              95

Lys Ser Phe Cys Ser Arg Gly Phe Leu Asp Ala Ala Asn Ser Phe
                100             105             110

Pro Glu Phe Gly Lys Leu Gly Ser Val Asp Asp Ser Lys Arg Glu Ile
            115             120             125

Ala Ala Phe Phe Ala His Val Thr His Glu Thr Gly His Phe Cys His
        130             135             140

Ile Glu Glu Ile Asn Gly Ala Ser His Asp Tyr Cys Asp Glu Gly Asn
145             150             155             160

Thr Gln Tyr Pro Cys Ala Pro Gly Lys Asn Tyr Phe Gly Arg Gly Pro
                165             170             175

Ile Gln Leu Thr Trp Asn Tyr Asn Tyr Gly Ala Ala Gly Asp Ala Leu
            180             185             190

Arg Leu Asn Leu Leu Gly Ser Pro Glu Met Val Ala Arg Asp Ala Ala
        195             200             205

Val Ser Phe Lys Thr Ala Leu Trp Phe Trp Met Lys Asn Val Arg Pro
    210             215             220

Val Ile Asn Gln Gly Phe Gly Ala Thr Ile Arg Ala Ile Asn Gly Ala
225             230             235             240

Ile Glu Cys Asn Gly Gly Asn Pro Gly Thr Val Gln Ala Arg Ile Gly
                245             250             255

Tyr Tyr Arg Asp Tyr Cys Ala Lys Phe Gly Val Ala Pro Gly Glu Asn
            260             265             270

Leu Ser Cys
```

The underlined 28-amino acid fragment at the N terminus in SEQ ID NO: 2 represents the signal sequence (SEQ ID NO: 12). The rest 247-amino acid sequence is the mature form of the chitinase (SEQ ID NO: 10). A conservative motif VSFK-TALWFWM (SEQ ID NO: 14) is underlined and shown in bold. The corresponding nucleotide sequences encoding SEQ ID NOs: 10, 12, and 14 (i.e., SEQ ID NOs: 9, 12, and 13) can be found in SEQ ID NO: 1 listed above. Shown below is a 1002 bp cDNA sequence (SEQ ID NO: 8) encoding the above-described chitinase.

```
                                                        SEQ ID NO: 8
aagcagtggt aacaacgcag agtacgcggg gcccacaaga acatccctta atttctcctt    60
ctccaatctc caaagagaaa gaaatgtcgc caaacaatgt cgccaaacaa tgccttactc   120
ctttctcttc ccctccttgt ttccttgctc atttcggcca tgcccagacc agtaacgagc   180
cagaactgtg gctgtgcgcc caacttatgt tgtagcaggt tcgggttctg tggccagggc   240
gaggcgtatt gcggcgaggg atgccgggaa ggtccatgca ataagccgtc gcctactcct   300
ggcggcggca gttcacttgc agagatcgtc actcccgatt tcttcaacgg aataattaat   360
caagcggctg ccggctgtgc cgggaagagt ttttgctcgc gaggtggctt tctagatgct   420
gctaattcgt ttcccgaatt tggaaaactt ggttcagtcg atgattctaa gcgtgagatt   480
gctgcgtttt tcgctcatgt cacccatgaa actggacatt tttgtcacat cgaagaaata   540
aatggagctt ctcatgacta ttgcgacagg ggaaacacac aatacccttg tgcaccaggg   600
aagaactact tcggccgagg accgattcag ctaacatgga attacaacta cggagcagcc   660
ggtgatgcct tgaggctcaa cttgttaggc tcgccggaga tggtggcaag agatgctgca   720
gtttccttca agacagcctt gtggttttgg atgaagaatg tccggccggt gatcaaccaa   780
gggttcggtg caaccattcg agccatcaac ggtgcaatag agtgcaatgg gggaaatcca   840
```

-continued

```
ggaactgttc aggctcgtat tggttattat agagattatt gtgctaaatt tggtgttgct    900
cctggtgaaa atctcagttg ttaattactt attatgtcta atagtttcct atttgagca     960 aatgaaggga aagaaaaata aaataaaata atatattttt tt                      1002
```

(underlined part = open reading frame, i.e., SEQ ID NO: 1)

Accordingly, one aspect of this invention features an isolated polypeptide containing a sequence that is at least 70% (e.g., 75%, 80%, 85%, 90%, 95%, 99%, or 100%) identical to SEQ ID NO: 10 or 2. In one example, the sequence contains SEQ ID NO: 14. Preferably, the sequence contains SEQ ID NO: 10 or 2. An "isolated polypeptide" refers to a polypeptide substantially free from naturally associated molecules, i.e., it is at least 75% (i.e., any number between 75% and 100%, inclusive) pure by dry weight. Purity can be measured by any appropriate standard method, for example, by column chromatography, polyacrylamide gel electrophoresis, or HPLC analysis. An isolated polypeptide of the invention can be purified from a natural source, produced by recombinant DNA techniques, or by chemical methods.

The invention also features an isolated nucleic acid that contains a sequence encoding one of the above-mentioned polypeptides or a complement thereof. Examples of the nucleic acid include those having SEQ ID NO: 13, 9, or 1, as well as those that are at least 70% (e.g., 75%, 80%, 85%, 90%, 95%, 99%, or 100%) identical to SEQ ID NO: 13, 9, or 1. A nucleic acid refers to a DNA molecule (e.g., a cDNA or genomic DNA), an RNA molecule (e.g., an mRNA), or a DNA or RNA analog. A DNA or RNA analog can be synthesized from nucleotide analogs. The nucleic acid molecule can be single-stranded or double-stranded, but preferably is double-stranded DNA. An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. The nucleic acid described above can be used to express a polypeptide of this invention. For this purpose, one can operatively linked the nucleic acid to suitable regulatory sequences to generate an expression vector.

A vector refers to a nucleic acid molecule capable of transporting another nucleic acid to which it has been linked. The vector can be capable of autonomous replication or integrate into a host DNA. Examples of the vector include a plasmid, cosmid, or viral vector. The vector of this invention includes a nucleic acid in a form suitable for expression of the nucleic acid in a host cell. Preferably the vector includes one or more regulatory sequences operatively linked to the nucleic acid sequence to be expressed. A "regulatory sequence" includes promoters, enhancers, and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vector can be introduced into host cells to produce the polypeptide of this invention.

Also within the scope of this invention is a host cell that contains the above-described nucleic acid. Examples include *E. coli* cells, insect cells (e.g., using baculovirus expression vectors), yeast cells, plant cells, or mammalian cells. To produce a polypeptide of this invention, one can culture a host cell in a medium under conditions permitting expression of the polypeptide encoded by a nucleic acid of this invention, and purify the polypeptide from the cultured cell or the medium of the cell. Alternatively, the nucleic acid of this invention can be transcribed and translated in vitro, for example, using T7 promoter regulatory sequences and T7 polymerase.

Another aspect of this invention features a composition containing the isolated polypeptide described above or a functional equivalent thereof. The composition can be a pharmaceutical composition (e.g., an antifungal composition or an antibacterial composition) that contains a pharmaceutically acceptable carrier. It can also be a dietary composition, such as tea, soft drink, juice, milk, coffee, jelly, ice cream, yogurt, cookie, cereal, chocolate, snack bar, candy, chewing gum, syrup, or food capsule. The composition can also be a topical composition and contains a cosmetically acceptable carrier.

The polypeptides and compositions described above can be used for various purposes. For example, one can use them to degrade a structure containing chitin by contacting the structure with an effective amount of the polypeptide or composition. The structure can be a cell wall of a fungus or a bacterium. One can also use the polypeptides and compositions to inhibit growth of microbes by contacting one or more microbes with an effective amount of the polypeptide or composition. The microbes can be bacteria or fungi. Examples of the bacteria or fungi includes, but not limited to, *Rhizoctonia solani*, *Phytophthora* sp., *Sclerotium rolfsii*, *Alternaria brassicicola*, *Fusarium lateritium*, and *Sclerotium rolfsii*. One can also use them as biocides to control plant pathogens. Accordingly, this invention features a method for preventing the growth of one or more microbes on a part of a plant. The method includes contacting the part of the plant with an effective amount of the polypeptide or composition.

In another aspect, this invention features a transformed cell containing a heterologous polynucleotide containing a nucleic acid encoding one of the above-described polypeptides. The transformed cell can be made by conventional methods and used to generate a transgenic plant whose genome comprises a heterologous polynucleotide containing the nucleic acid. Transgenic plants thus-generated are resistant to various plant pathogens. A heterologous polypeptide, nucleic acid, or gene is one that originates from a foreign species, or, if from the same species, is substantially modified from its original form. Two fused domains or sequences are heterologous to each other if they are not adjacent to each other in a naturally occurring protein or nucleic acid.

Other features or advantages of the present invention will be apparent from the following detailed description, and also from the claims.

DETAILED DESCRIPTION

This invention relates to a novel class IV chitinase from a papaya fruit chitinase, CpCHI. As shown below, this chitinase has a wide optimal pH values, long-term stability, and strong antifungal activity against various fungi. Thus, CpCHI can be used, among others, as a bio-control agent to protect plants against agriculture pathogens.

A chitinase of this invention or its variant can be produced by using an expression vector that contains an isolated nucleic acid of this invention. The vector can be designed for expression of a chitinase in prokaryotic or eukaryotic cells, such as bacterial cells (e.g., *E. coli*), yeast cells (e.g., *P. pastoris*), insect cells, plant cells, and mammalian cells. Suitable host cells are known in the art. See, e.g., Goeddel, (1990) *Gene Expression Technology: Methods in Enzymology* 185, Academic Press, San Diego, Calif. Expression of a chitinase can be carried out with vectors containing constitutive or inducible promoters directing the expression of either a fusion or a non-fusion chitinase. Fusing a tag to the amino or carboxyl terminus of a chitinase facilitates purification of soluble chitinase. Examples of a tag include multiple histidines, glutathione S-transferase (GST), maltose E binding protein, protein A, and suitable peptide epitopes, e.g., HA, Myc, and FLAG. In view of anti-fungus and anti-bacterium activity, it is preferred that the recombinant chitinase is fused to one or more the tag proteins, thereby minimizing effects on the host cells.

A vector can be introduced into host cells via conventional transformation or transfection techniques, such as calcium phosphate or calcium chloride co-precipitation, DEAE-dextran-mediated transfection, lipofection, or electroporation. After being transformed or transfected with a vector of this invention, a host cell can be cultured in a medium to express a chitinase. The expressed chitinase can then be isolated from the host cell or from the culture medium using standard techniques before be tested for its enzymatic activity by conventional methods or methods descried in the examples below.

If an expressed chitinase is fused to one of the tags described above, the chitinase can be easily purified from a clarified cell lysate or culture medium with an appropriate affinity column, e.g., $Ni^{2+}$ NTA resin for hexa-histidine, glutathione agarose for GST, amylose resin for maltose binding protein, and antibody affinity columns for epitope tagged proteins. The chitinase can be eluted from the affinity column, or if appropriate, cleaved from the column with a site-specific protease. If the chitinase is not tagged for purification, routine methods in the art can be used to develop procedures to isolate it from cell lysates or the media. See, e.g., Scopes, R K (1994) Protein Purification: Principles and Practice, 3rd ed., New York: Springer-Verlag.

Polypeptides of this invention include functional variants or functional equivalents of the above-described chitinase, e.g., SEQ ID NO: 10 or 2. A functional equivalent of SEQ ID NO: 10 or 2 refers to a polypeptide derived from SEQ ID NO: 10 or 2, e.g., a fusion polypeptide or a polypeptide having one or more point mutations, insertions, deletions, truncations, or a combination thereof. It is at least 70% (e.g., 75%, 80%, 85%, 90%, 95%, 99%, or 100%) identical to SEQ ID NO: 10 or 2, and has the above-mentioned conservative motif VSFK-TALWFWM. The variants include biologically active fragments whose sequences differ from the chitinase described herein by one or more conservative amino acid substitutions or by one or more non-conservative amino acid substitutions, deletions, or insertions that do not abolish the catalytic activity.

Proteins that are functionally equivalent to a polypeptide of this invention can be encoded by DNA isolated through the above hybridization technique or by the gene amplification technique, normally have a high homology to the amino acid sequence of the CpCH1 protein. The proteins of the present invention also include proteins that are functionally equivalent to the protein, which also have a high homology with the protein comprising any one of the amino acid sequences of SEQ ID NO:2 or 10. High homology is defined normally as a homology of 70% or higher, favorably 80% or higher, more favorably 90% or higher, and most favorably 95% or higher. The homology or identity of a protein can be determined by the algorithm in Wilbur, W. J. and Lipman, D. J. Proc. Natl. Acad. Sci. USA 80: 726-730 (1983).

All of the functional equivalents have substantially the chitinase activity, i.e., to catalyze hydrolysis of chitin. This activity can be determined by the assays described in the examples below or any analogous assays. The amino acid composition of a chitinase of the invention may vary without disrupting the chitinase activity. For example, such a variant can contain one or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a polypeptide is preferably replaced with another amino acid residue from the same side chain family. Alternatively, mutations can be introduced randomly along all or part of a polypeptide of this invention, such as by saturation mutagenesis, and the resultant mutants can be screened for the chitinase activity to identify variants of this invention.

Within the scope of this invention is a composition that contains a suitable carrier and one or more of the polypeptides described above. The composition can be a pharmaceutical composition that contains a pharmaceutically acceptable carrier, a dietary composition that contains a dietarily suitable carrier, or a cosmetic composition that contains a cosmetically acceptable carrier.

The polypeptides and compositions can be used to inhibit growth of microbes, such as fungi. As disclosed in the examples below, the polypeptides can be used to control fungus growth on plants and protect plants against fungus infections.

Infection with pathogenic fungi caused as much as 20% loss of major food and cash crops. Among the fungi, *Sclerotium rolfsii* and *Rhizoctonia solani* are soil-borne fungi, which devastate plants in a wide range. These fungi infect seeds, seedlings, and mature plants in the field, causing collar rot, wilt, damping off, dry root rot, and the like. *Alternaria brassicicola* is considered a necrotrophic plant pathogenic fungus and has been shown to secrete numerous toxic secondary metabolites and proteins that cause cell death via induction of apoptosis in plants or by directly damaging cells. It causes black spot disease in a wide range of *Brassica* crops. Currently, a large number of chemical crop protectants that are used to control fungi are detrimental to the environment and human health. There is a need for safe and biodegradable protectants to control fungus growth.

Effecting the control may be accomplished simply by applying the polypeptides or composition to a plant tissue or to the plant or part of the plant. For example, if an infection occurs on the leaves, then spraying or dusting the leaves may accomplish that objective easily and efficiently. Alternatively uniform spraying or dusting to the part of the plant above ground may result control to the entire plant (i.e., stem and both sides of the leaves). If control on the roots is desired, application to the seeds or the soil around the seeds or roots is a possible method of regulation.

Depending on the kind of the composition, a carrier may be a suitable dietary carrier or a pharmaceutically acceptable carrier. Examples of a pharmaceutically acceptable carrier include, but are not limited to, biocompatible vehicles, adjuvants, additives, and diluents to achieve a composition usable as a dosage form. Examples of a dietary composition include, but are not limited to, foods, food additives, nutritional supplements, and pharmaceutical preparations for human or non-human animals (e.g., feed). It may be in the form of tablets, suspensions, implants, solutions, emulsions, capsules, powders, syrups, liquid compositions, ointments, lotions, creams, pastes, gels, or the like. A pharmaceutically acceptable carrier, after administered to or upon a subject, does not cause undesirable physiological effects. The carrier in the pharmaceutical composition must be "acceptable" also in the sense that it is compatible with the active ingredient and, preferably, capable of stabilizing it. One or more solubilizing agents can be utilized as pharmaceutical carriers for delivery of an active compound. Examples of other carriers include colloidal silicon oxide, magnesium stearate, cellulose, sodium lauryl sulfate, and D&C Yellow # 10. The above-described composition, in any of the forms described above, can be used for inhibiting growth of microbes and for treating infections or diseases caused by the microbes.

A polypeptide of this invention can be incorporated into pharmaceutical compositions alone or in combination with other anti-fungus or anti-bacterium agents into pharmaceutical compositions for prophylactic or therapeutic use in a subject that has or is at risk of an infection. For example, a pharmaceutical composition can include an effective amount of the polypeptide and a pharmaceutically acceptable carrier. Alternatively, a pharmaceutical composition can include an effective combined amount of the polypeptide and another anti-fungus or anti-bacterium agent. The term "effective amount" refers to the amount of an active composition that is required to confer a prophylactic or therapeutic effect on the treated subject. The term "effective combined amount" refers to the amount a combination of active compositions sufficient to confer a prophylactic or therapeutic effect on the treated subject, where the included amount of each active composition by itself would be insufficient to confer an adequate prophylactic or therapeutic effect or would cause an undesirable effect.

Similarly, a polypeptide of this invention can be incorporated into a topical composition. Such a topical composition contains a safe and effective amount of a dermatologically acceptable carrier suitable for application to the skin. Generally, a topical composition can be solid, semi-solid, cream, or liquid. It may be a cosmetic or dermatologic product in the form of an ointment, lotion, foam, cream, gel, or solution. Suitable dermatologically acceptable carriers are known in the art. See, e.g., Harry's Cosmeticology, 7th Ed., Harry & Wilkinson (Hill Publishers, London 1982); Pharmaceutical Dosage Forms—Disperse Systems; Lieberman, Rieger & Banker, Vols. 1 (1988) & 2 (1989); Marcel Decker, Inc.; The Chemistry and Manufacture of Cosmetics, 2nd. Ed., deNavarre (Van Nostrand 1962-1965); and The Handbook of Cosmetic Science and Technology, 1st Ed. Knowlton & Pearce (Elsevier 1993). The topical composition can be used to treat skin infections with microbes.

The term "treating" refers to the administration of an effective amount of a composition of the invention to a subject (such as a plant, a human, or a non-human animal) that has one of the above-described infections or conditions, a symptom of such a infections, or a predisposition toward such a infection or condition, with the purpose to confer a therapeutic effect, e.g., to cure, relieve, alter, affect, ameliorate, or slow down the infection or condition, the symptom of it, or the predisposition toward it.

The following specific examples are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Example 1

Cloning, Sequencing, and Identification of Papaya CpCHI cDNA

Papaya (*Carica papaya* L. cv. Tainong 2) fruits, flowers, and leaves were harvested from a local orchard at different development stages, and immediately frozen and stored at −80° C. until use. Oligonucleotide primers were purchased from DNAFax (Taipei, Taiwan).

Total RNA was extracted from papaya samples by the Pine Tree method (Chang et al., 1993 Plant Mol Biol Rep 11, 113-116). The poly(A)+ RNA was isolated from the total RNA with an Oligotex mRNA Kit (Qiagen Inc., CA). The cDNA was synthesized using a CapFinder PCR Library Construction kit. For cloning differentially expressed cDNA, a PCR-based subtractive hybridization kit was used (Clontech Lab., CA, USA).

Papaya cDNAs derived from both ripe and immature fruits were used in subtractive hybridization (Clontech, PCR-Select cDNA subtraction kit) according to the procedure described in Wang et al., 1991, Proc. Natl. Acad. Sci. U.S.A. 88: 11505-11509. cDNAs from the immature fruits served as the driver, and those from the ripe fruits served as the tester. The subtractive hybridization was intended to enrich cDNAs that are up-regulated in ripe papaya fruit. The CapFinder PCR method (Clontech) was used to isolate the 5' and 3' ends of important cDNA inserts, according to the protocols provided by the manufacturer.

The Cp-chi-R1 primer (5'CGAATTAGCAGCATCTA-GAAAGCCACCTCG 3', SEQ ID NO: 3) was synthesized according to the sequence of a papaya chitinase derived from the subtractive hybridization. DNA of 0.4 kb was amplified by using the CapFinder PCR technique to obtain its 5'-end. Cp-chi-1 primer (5'-ATGCAGAACTGTGGCTGT GCG, SEQ ID NO: 4) and Cp-chi-2 primer (5'-ACAACT-GAGATTTTCACCAGGAG, SEQ ID NO: 5) were used to amplify the full length of papaya chitinase cDNA. The 0.81 kb full length cDNA was obtained. All the PCR amplified fragments were subcloned into pGEM-T easy vector (Promega) using *Escherichia coli* DH5α as host. The nucleotide sequence was determined by autosequencing (ABI PRISM BigDye Terminator Cycle Sequencing Ready Reaction kits, Perkin-Elmer Co., CA) using an ABI PRIZM 377 DNA sequencer.

The results showed that a novel papaya fruit chitinase CpCHI cDNA was isolated. Its full length was 1002 bp in length and contained an open reading frame of 825 bp. The deduced 275-amino acid polypeptide had a predicted molecular mass and isoelectric point of 29.1 kDa and 6.59, respectively. According to the CBS Prediction Servers SignalP-NN prediction (at www.cbs.dtu.dk/services), the CpCHI polypeptide contains a 28 amino-acid signal peptide at the N-terminus. The predicated molecular mass of mature CpCHI was 26.2 kDa, with an isoelectric point of 6.32. Comparing the CpCHI polypeptide with known sequences indicated that the CpCHI polypeptide was most similar to *Arabidopsis thaliana* chitinase (Y14590) with 63% identity and 78% similarity.

A phylogenetic tree was constructed from the deduced amino acid sequences of CpCHI and chitinases from other species in the database using the PROTDIST and NEIGHBOR programs of the Phylip software. It was found that CpCHI belonged to the same subgroup with other class IV chitinases, i.e., BvCHI, AtCHI, VvCHI1, and VvCHI2.

Example 2

Purification and Characterization of Recombinant CpCHI

Recombinant CpCHI proteins were generated by the recombinant DNA technology. The proteins were then analyzed for its activity.

Twenty nanograms of CpCHI cDNA was used as a template. Ten micromolar of the Cp-chi-N primers (5'-GGAAT-TCCATATGCAGAACTGTGGCTGTGCG, SEQ ID NO: 6) and the Cp-chi-C primer (5'-CCGCTCGAGACAACT-GAGATTTTCACCA GGAG, SEQ ID NO: 7) were used to obtain 0.75 kb cDNA, which encoded the mature protein and had Nde I or Xho I sites at the N or C terminal. The DNA fragment was then ligated with a pGEM-T easy vector (Promega) and transformed into *E. coli* DH5α host cells. Plasmid DNA was digested with NdeI and Xho I, and then was run as 1% agarose. The 0.75 kb insert DNA was recovered and ligated to a pET-20b (+) vector (Novagen), which was pre-digested with Nde I and Xho I. The resulting recombinant plasmid was transformed into *E. coli* Tunner (DE3).

The transformed *E. coli* cells were grown at 37° C. in a Luria Bertani (LB) medium containing 100 μg mL$^{-1}$ ampicillin until A600 reached 0.6. After 0.5 mM Isopropyl-D-thiogalactopyranoside (IPTG) was added, the culture was incubated at 37° C. for another 5 hours at 150 rpm. The bacterial cells and the insoluble cell debris for inclusion body purification were washed with the BugBuster reagent (Novagen) and harvested by centrifugation as described in the manual. The resulting inclusion body pellet was resuspended in a binding buffer (5 mM imidazole, 0.5 M NaCl, 20 mM Tris-HCl, pH 7.9, and 6 M urea). The CpCHI protein, which contained a 6×His tag at its N-terminus, was purified using Ni-NTA agarose (Qiagen QIAexpress). Briefly, the supernatant was applied into a Ni-NTA resin column. After washing with a buffer (60 mM imidazole, 0.5 M NaCl, 20 mM Tris-HCl, pH 7.9, and 6 M urea), CpCHI was recovered by an elution buffer (1 M imidazole, 0.5 M NaCl, 20 mM Tris-HCl, pH 7.9, and 6 M urea). Finally, the purified CpCHI was dialyzed in a TE buffer (10 mM Tris-HCl, 1 mM EDTA, pH 7.5) for further activity assay.

For gel activity staining, recombinant CpCHI was mixed with a gel loading buffer without β-mercaptoethanol and electrophoresed in a 12% polyacrylamide gel containing 0.1% glycol-chitin according to the method described in Trudel et al., 1989, Anal Biochem. 178, 362-366. After electrophoresis, the gel was washed with a buffer containing 100 mM sodium acetate, pH 5.0, 1% Triton X-100, and 1% skimmed milk at 37° C. for 1~2 hours, and then stained with 0.01% Calcoflour white M2R (Sigma) in 0.5 M Tris-HCl, pH 8.9 for 5~10 minutes. The gel was then exposed under UV.

Chitinase activity was generally measured using glycol chitin as a substrate. All enzymes other than CpCHI, were purchased from Promega (Madison, Wis.). Chemicals were purchased from Merck (Darmstadt, Germany). An enzyme solution (10 μL) was added to 100 μL of 1% (w/v) glycol-chitin dissolved in 90 μL of a sodium acetate buffer (100 mM, pH 5.0), and was incubated at 30° C. for 3 hours. The reducing end group produced was measured calorimetrically at 420 nm with 200 μL of a potassium ferricyanide ($K_3Fe(CN)_6$) reagent according to the method descried in Boller et al., 1983, Planta. 157, 22-31. Reduced sugar levels were determined relative to N-acetyl-β-D-glucosamine standards of 0-150 μg mL$^{-1}$. One unit of chitinase activity is defined as the amount of enzyme producing 1 μmol reducing sugar per minute at 30° C. Substrate and enzyme blanks were also prepared in which the enzyme or substrate was incubated with a buffer. All measured values of absorbency were normalized against appropriate blank absorbencies. In this example, collodial chitin and chitosan were also used as substrate for subtract specificity analysis.

The optimal pH of the chitiolytic activity of CpCHI was determined by incubating the purified recombinant enzyme (5 μg) at different pH (3-10) at 30° C. for 3 hours using glycol chitin as the substrate. An acetate buffer (100 mM) was used for pH 3-5, a phosphate buffer (100 mM) for pH 6~7, a Tris-HCl buffer (100 mM) for pH 8, and a glycine-NaOH buffer for pH 9 and 10. The optimal temperature was determined by incubating the purified chitinase (5 μg) at different temperatures (10~90° C.) at pH 6.0 for 3 hours using glycol chitin as the substrate. The highest activity was calculated as relative activity (RA) 100%.

It was found that purified CpCHI appeared as a major band of 26.2 kDa on SDS-PAGE. After dialysis, the recombinant protein was tested for chitinase activity using the gel activity assay with glycol chitin as substrate. Its specific activity was found to be 14.8 U mg$^{-1}$ by spectrophtometric assay.

It was also found that the optimal condition for the enzyme activity of the recombinant CpCHI was 30° C. and pH 6.0, while the enzyme appeared to have broad pH optima between pH 5.0-9.0. The subtract specificity of the recombinant CpCHI was also tested on various chitinous subtracts (see Table 1).

TABLE 1

| Relative Activity of CpCHI toward Different Subtracts | |
|---|---|
| Subtract | Relative activity |
| Glycol chitin | 100 |
| Collodial chitin | 58.67 ± 5.03 |
| Chitosan | 11.33 ± 2.52 |

As shown in Table 1, recombinant CpCHI had highest activity toward glycol chitin (100%), and 59% and 11% activity toward colloidal chitin and chitosan, respectively.

The pH stability of recombinant CpCHI was determined. Briefly, purified recombinant CpCHI was incubated in buffers with pH from 3.0 to 10.0 at 30° C. for 3 hours. The residual activity was then determined at a standard condition (30° C. for 3 hours at pH 6.0). The results were averaged from three independent experiments. It was found that, at pH 5.0 to 9.0, the enzyme was stable and had at least 90% activity.

Effects of temperature on the CpCHI enzyme were examined. It was found that CpCHI maintained about at least 80% activity at temperatures between 10-50° C.

The stability of recombinant CpCHI during long-term storage was examined. It was found that the purified recombinant CpCHI was stable for long-term storage. The enzyme retained more than 60% of its activity for 3 weeks at 30° C. and more than 50% activity for 3 weeks at 37° C. The results were also averaged from three independent experiments. These unexpected findings indicated that recombinant CpCHI is suitable as a biocontrol agent.

Example 3

HPLC Analysis of Chitin Hydrolysis by CpCHI

Chitin hydrolysis was carried out in a phosphate buffer (100 mM, pH 6) at 30° C. with shaking. The concentrations of chitinase and glycol chitin suspension were 750 ng $\mu L^{-1}$ and 100 $\mu g\ mL^{-1}$, respectively. The reactions were quenched with 10% (v/v) acetic acid. Following a centrifugation at 5° C., the supernatant containing chitooligosaccharide products formed after 5 minutes was immediately injected into a 4.6 mm ID×250 mm L, Asahipak NH2P-50 4E column. The column was connected to an Agilent Technologies 1100 series HPLC system under the control of a Thermo Finnigan LCQ DECA electrospray mass spectrometer. The mass-to-charge ratios (m/z) of the expected oligosaccharides were selected as follows: Glc-NAc (221.9), $(GlcNAc)_2$ (425.5), $(GlcNAc)_3$ (627.6), $(GlcNAc)_4$ (830.8), $(GlcNAc)_5$ (1034.0), $(GlcNAc)_6$ (1237.2), and $(GlcNAc)_7$ (1440.0).

It was found that the hydrolyzed products were $(GlcNAc)_2$ and (GlcNAc). This result differed from other exochitinases or endochitinases, which produced $(GlcNAc)_2$ only or a series of $(GlcNAc)_2$, $(GlcNAc)_3$, or $(GlcNAc)_4$, respectively (Kasprzewska, 2003, Cell. Mol. Biol. Let. 8, 809-824.10). In order to elucidate the reaction mechanism, the products of hydrolytic reaction of glycol chitin were further analyzed at different time points. It was found that the hydrolyzed product was $(GlcNAc)_3$ after 1 hour, and $(GlcNAc)_3$, $(GlcNAc)_2$, and (GlcNAc) after 2 hours. The final, hydrolyzed products were $(GlcNAc)_2$ and (GlcNAc), and there was no $(GlcNAc)_3$. This result suggests that CpCHI is a novel type of chitinase which has an initially exochitinase activity that yields $(GlcNAc)_3$, and then when the $(GlcNAc)_3$ is accumulated, the $(GlcNAc)_3$ is further cleaved into $(GlcNAc)_2$ and (GlcNAc).

Example 4

Effect of Various Reagents and Cations

To analyze the effect of metals and other factors on chitinase activity, the enzyme was preincubated with a 10 mM of different metals and inhibitors. After 30 minutes, the remaining chitinase activity was measured in the manner described above. The results are shown in Table 2.

TABLE 2

Effect of Various Reagents and Cations on the Chitinase Activity of CpCHI

| Reagents and Cations | Relative activity (%) |
|---|---|
| None | 100 |
| EDTA | 93.33 ± 3.06 |
| KCl | 92.33 ± 1.53 |
| $AgNO_3$ | 83.67 ± 2.52 |
| $CuSO_4$ | 40.00 ± 7.2 |
| $ZnSO_4$ | 38.00 ± 3.61 |
| $MnCl_2$ | 35.33 ± 3.06 |
| $HgCl_2$ | 0 |
| $FeCl_3$ | 70.67 ± 3.06 |

As shown in Table 2, $K^+$, $Ag^+$, $Fe^{3+}$, and EDTA slightly reduced CpCHI activity. At a concentration of 10 mM, they reduced the activity by 7.67%, 16.33%, 29.33%, and 6.67%, respectively. In contrast, some divalent metal ions reduced CpCHI activity more significantly. Specifically, CpCHI activity was inhibited by 64.7%, 62.0%, and 60% in the presence of 10 mM $Mn^{2+}$, $Zn^{2+}$, and $Cu^{2+}$. It was found that 10 mM $Hg^{2+}$ inhibited the chitiolytic activity of CpCHI completely.

Example 5

Antifungal Activity of CpCHI

The antifungal activity of recombinant chitinase protein was assessed by the hypha extension inhibition assay. *Sclerotium rolfsii* and *Phytophthora* sp. were provided from Hualien District Agricultural Research and Extension Station. *Rhizoctonia solani* and *Alternaria brassicicola* were provided by Dr. Jenn-Wen Hung of the Department of Plant Pathology of National Chung-Hsing University. A disc of each strain of fungus was removed from an actively growing fungal culture, and placed in the center of a fresh potato dextrose agar plate. After incubation at room temperature for 3 to 4 days, the recombinant chitinase or a control buffer (10 mM Tris-HCl pH7.5, 1 mM EDTA) were separately applied into a pool, which was 1 cm from the perimeter. The inhibition of the hypha extension was detected as a crescent-shaped zone of inhibition around the peripheral disc as the fungus grew out from the central disc.

The effects of recombinant CpCHI on the growth of *Phytophthora* sp., *Sclerotium rolsii*, and *Rhizoctonia solani* were examined using standard methods. Disease resistance assays were carried out using detached leaves of cabbage, bell pepper, and tomato that were inoculated with each of the pathogens. Cabbage (*Brassica oleracea*), bell pepper (*Capsicam annuum*), and tomato (*Solanum lycopersicum*) were obtained from Known-You Seed CO., LTD. An agar plug containing the pathogen was placed on the center of leaves. At day 1 day after inoculation, the detached leaves began to show lesions surrounded by yellow halos. Then, different solutions, including $H_2O$, a TE buffer (10 mM Tris-HCl pH 7.5, 1 mM EDTA), or 5, 10, 15 µM CpCHI in the TE buffer was sprayed onto the leaves. At day 4 after inoculation, the pathogenesis inhibition by 5, 10, or 15 µM CpCHI was about 37%, 83%, and 98%, respectively (Table 3). It was found that recombinant CpCHI showed great antifungal activity against *Phytophthora* sp., *Sclerotium rolfsi*, and *Rhizoctonia solani*. Also, recombinant CpCHI inhibited the growth of these three fungi with as little as 15 µM, and the inhibited activity lasted for 7 days.

These results suggest that recombinant CpCHI is effective in protecting the leaves against Southern blight.

TABLE 3

Effects of CpCHI on Detached Leaves against *Sclerotium rolfsii*

| | Percentage of the symptom appearing | | |
|---|---|---|---|
| | Cabbage | bell pepper | tomato |
| H2O | 100 | 100 | 100 |
| TE buffer | 97.67 ± 2.52 | 100 | 98.67 ± 2.31 |
| 5 μM CpCHI | 55.33 ± 6.11 | 66.67 ± 7.34 | 65 ± 15 |
| 10 μM CpCHI | 14.33 ± 5.13 | 23.33 ± 7.64 | 13.33 ± 10.41 |
| 15 μM CpCHI | 1.66 ± 2.88 | 3.33 ± 2.77 | 1.66 ± 1.32 |

Assays were also carried out to examine effects of CpCHI on *Alternaria brassicicola*, a fungus isolated from cabbages. The fungus was cultured in potato dextrose agar (DIFCO) for 2 weeks. After sporulation, the spores of the fungus were suspended in water to a concentration of $10^4$ spores $mL^{-1}$. A fungal spore stock (approximately 500 spores) was cultured at 24° C. for 24 hours in the following solutions: (A) $H_2O$, (B) TE buffer (10 mM Tris-HCl pH 7.5, 1 mM EDTA), (C) 5 μM CpCHI in TE buffer, and (D) 10 μM CpCHI in TE buffer. The inhibition of spore germination was examined under a light microscope at 200× amplification (Li et al., 2003, Plant Cell Physiol. 44, 1162-1167). The percentage of germination was calculated from 10 different observations. All experiments were conducted in triplicates.

It was found that 5 μM and 10 μM recombinant CpCHI inhibited spore germination significantly by 50% and 98%, respectively.

Example 6

Antibacterial Activity of CpCHI

Experiments were conducted to examine recombinant CpCHI's ability to suppress the growth of *E. coli* ED2566 or *E. coli* AD494. Briefly, the *E. coli* strain was grown at 37° C. in an LB medium with shaking at 225 rpm overnight. Then, the overnight culture was 100× diluted in a fresh LB medium containing 1 μM, 1.5 μM, 2 μM, 2.5 μM, or 3 μM CpCHI. A TE buffer (10 mM Tris-HCl pH7.5, 1 mM EDTA) was used as a control. Changes in density at 600 nm were monitored. The assays were conducts in triplicates and the average were recorded to examine the inhibition of bacterial growth. It was found that CpCHI suppressed the growth of *E. coli* ED2566 and *E. coli* AD494 and that its $IC_{50}$ was about 2.5 μM.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

---

What is claimed is:

1. An isolated nucleic acid comprising a nucleotide sequence encoding a polypeptide having chitinase activity and comprising an amino acid sequence that is 90% identical to SEQ ID NO: 10 or the full complement thereof.

2. The nucleic acid of claim 1, wherein the nucleic acid contains the sequence of SEQ ID NO: 13.

3. The nucleic acid of claim 2, wherein the nucleic acid contains the sequence of SEQ ID NO: 9.

4. The nucleic acid of claim 3, wherein the nucleic acid contains the sequence of SEQ ID NO: 1.

5. An expression vector comprising the nucleic acid of claim 1.

6. A cultured host cell comprising the nucleic acid of claim 1.

7. A method of producing a polypeptide having chitinase activity, comprising culturing the host cell of claim 6 in a medium under conditions permitting expression of said polypeptide encoded by the nucleic acid, and purifying the polypeptide from the cultured cell or the medium of the cell.

8. A cultured transformed cell comprising a heterologous polynucleotide containing the nucleic acid of claim 1.

9. The nucleic acid of claim 1, wherein the polypeptide comprises the sequence of SEQ ID NO:10.

* * * * *

SEQUENCE LISTING

<160> NUMBER OF SEQ ID NOS: 15

<210> SEQ ID NO 1
<211> LENGTH: 827
<212> TYPE: DNA
<213> ORGANISM: Carica papaya

<400> SEQUENCE: 1

```
atgtcgccaa acaatgcctt actcctttct cttcccctcc ttgtttcctt gctcatttcg      60
gccatgccca gaccagtaac gagccagaac tgtggctgtg cgcccaactt atgttgtagc     120
aggttcgggt tctgtggcca gggcgaggcg tattgcggcg agggatgccg ggaaggtcca     180
tgcaataagc cgtcgcctac tcctggcggc ggcagttcac ttgcagagat cgtcactccc     240
gatttcttca acggaataat taatcaagcg gctgccggct gtgccgggaa gagtttttgc     300
tcgcgaggtg gctttctaga tgctgctaat tcgtttcccg aatttggaaa acttggttca     360
gtcgatgatt ctaagcgtga gattgctgcg tttttcgctc atgtcaccca tgaaactgga     420 cattttgtc acatcgaaga aataaatgga gcttctcatg actattgcga cgagggaaac     480
acacaatacc cttgtgcacc agggaagaac tacttcggcc gaggaccgat tcagctaaca     540
tggaattaca actacggagc agccggtgat gccttgaggc tcaacttgtt aggctcgccg     600
gagatggtgg caagagatgc tgcagtttcc ttcaagacag ccttgtggtt ttggatgaag     660
aatgtccggc cggtgatcaa ccaagggttc ggtgcaacca ttcgagccat caacggtgca     720
atagagtgca atggggaaa tccaggaact gttcaggctc gtattggtta ttatagagat     780
tattgtgcta aatttggtgt tgctcctggt gaaaatctca gttgtta                    827
```

```
<210> SEQ ID NO 2
<211> LENGTH: 275
<212> TYPE: PRT
<213> ORGANISM: Carica papaya

<400> SEQUENCE: 2

Met Ser Pro Asn Asn Ala Leu Leu Ser Leu Pro Leu Leu Val Ser
 1               5                  10                  15

Leu Leu Ile Ser Ala Met Pro Arg Pro Val Thr Ser Gln Asn Cys Gly
            20                  25                  30

Cys Ala Pro Asn Leu Cys Cys Ser Arg Phe Gly Phe Cys Gly Gln Gly
        35                  40                  45

Glu Ala Tyr Cys Gly Glu Gly Cys Arg Glu Gly Pro Cys Asn Lys Pro
    50                  55                  60

Ser Pro Thr Pro Gly Gly Ser Ser Leu Ala Glu Ile Val Thr Pro
65                  70                  75                  80

Asp Phe Phe Asn Gly Ile Ile Asn Gln Ala Ala Gly Cys Ala Gly
                85                  90                  95

Lys Ser Phe Cys Ser Arg Gly Gly Phe Leu Asp Ala Ala Asn Ser Phe
            100                 105                 110

Pro Glu Phe Gly Lys Leu Gly Ser Val Asp Asp Ser Lys Arg Glu Ile
        115                 120                 125

Ala Ala Phe Phe Ala His Val Thr His Glu Thr Gly His Phe Cys His
    130                 135                 140

Ile Glu Glu Ile Asn Gly Ala Ser His Asp Tyr Cys Asp Glu Gly Asn
145                 150                 155                 160

Thr Gln Tyr Pro Cys Ala Pro Gly Lys Asn Tyr Phe Gly Arg Gly Pro
                165                 170                 175

Ile Gln Leu Thr Trp Asn Tyr Asn Tyr Gly Ala Ala Gly Asp Ala Leu
            180                 185                 190

Arg Leu Asn Leu Leu Gly Ser Pro Glu Met Val Ala Arg Asp Ala Ala
        195                 200                 205

Val Ser Phe Lys Thr Ala Leu Trp Phe Trp Met Lys Asn Val Arg Pro
    210                 215                 220

Val Ile Asn Gln Gly Phe Gly Ala Thr Ile Arg Ala Ile Asn Gly Ala
225                 230                 235                 240

Ile Glu Cys Asn Gly Gly Asn Pro Gly Thr Val Gln Ala Arg Ile Gly
                245                 250                 255

Tyr Tyr Arg Asp Tyr Cys Ala Lys Phe Gly Val Ala Pro Gly Glu Asn
            260                 265                 270

Leu Ser Cys
        275

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgaattagca gcatctagaa agccacctcg                                          30

<210> SEQ ID NO 4
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 4
atgcagaact gtggctgtgc g                                              21

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acaactgaga ttttcaccag gag                                            23

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggaattccat atgcagaact gtggctgtgc g                                   31

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccgctcgaga caactgagat tttcaccagg ag                                  32

<210> SEQ ID NO 8
<211> LENGTH: 1002
<212> TYPE: DNA
<213> ORGANISM: Carica papaya

<400> SEQUENCE: 8
aagcagtggt aacaacgcag agtacgcggg gcccacaaga acatcccta atttctcctt      60 ctccaatctc caaagagaaa gaaatgtcgc caaacaatgt cgccaaacaa tgccttactc    120
ctttctcttc ccctccttgt ttccttgctc atttcggcca tgcccagacc agtaacgagc    180
cagaactgtg gctgtgcgcc caacttatgt tgtagcaggt tcgggttctg tggccagggc    240
gaggcgtatt gcggcgaggg atgccgggaa ggtccatgca taagccgtc gcctactcct     300 ggcggcggca gttcacttgc agagatcgtc actcccgatt tcttcaacgg aataattaat    360
caagcggctg ccggctgtgc cgggaagagt ttttgctcgc gaggtggctt tctagatgct    420
gctaattcgt ttcccgaatt tggaaaactt ggttcagtcg atgattctaa gcgtgagatt    480
gctgcgtttt tcgctcatgt cacccatgaa actggacatt tttgtcacat cgaagaaata    540
aatggagctt ctcatgacta ttgcgacgag ggaaacacac aatacccttg tgcaccaggg    600
aagaactact cggccgagg accgattcag ctaacatgga attacaacta cggagcagcc     660
ggtgatgcct tgaggctcaa cttgttaggc tcgccggaga tggtggcaag agatgctgca    720
```

```
gtttccttca agacagcctt gtggttttgg atgaagaatg tccggccggt gatcaaccaa    780
gggttcggtg caaccattcg agccatcaac ggtgcaatag agtgcaatgg gggaaatcca    840
ggaactgttc aggctcgtat tggttattat agagattatt gtgctaaatt tggtgttgct    900
cctggtgaaa atctcagttg ttaattactt attatgtcta atagtttcct atttgagaca    960
aatgaaggga agaaaaaata aaataaaata atatattttt tt                      1002
```

<210> SEQ ID NO 9
<211> LENGTH: 743
<212> TYPE: DNA
<213> ORGANISM: Carica papaya

<400> SEQUENCE: 9

```
cagaactgtg gctgtgcgcc caacttatgt tgtagcaggt tcgggttctg tggccagggc     60
gaggcgtatt gcggcgaggg atgccggaaa ggtccatgca ataagccgtc gcctactcct    120
ggcggcggca gttcacttgc agagatcgtc actcccgatt tcttcaacgg aataattaat    180
caagcggctg ccggctgtgc cgggaagagt ttttgctcgc gaggtggctt tctagatgct    240
gctaattcgt ttcccgaatt tggaaaactt ggttcagtcg atgattctaa gcgtgagatt    300
gctgcgtttt tcgctcatgt cacccatgaa actggacatt tttgtcacat cgaagaaata    360
aatggagctt ctcatgacta ttgcgacgag ggaaacacac aatacccttg tgcaccaggg    420
aagaactact tcggccgagg accgattcag ctaacatgga attacaacta cggagcagcc    480
ggtgatgcct tgaggctcaa cttgttaggc tcgccggaga tggtggcaag agatgctgca    540
gtttccttca agacagcctt gtggttttgg atgaagaatg tccggccggt gatcaaccaa    600
gggttcggtg caaccattcg agccatcaac ggtgcaatag agtgcaatgg gggaaatcca    660
ggaactgttc aggctcgtat tggttattat agagattatt gtgctaaatt tggtgttgct    720
cctggtgaaa atctcagttg tta                                            743
```

<210> SEQ ID NO 10
<211> LENGTH: 247
<212> TYPE: PRT
<213> ORGANISM: Carica papaya

<400> SEQUENCE: 10

```
Gln Asn Cys Gly Cys Ala Pro Asn Leu Cys Cys Ser Arg Phe Gly Phe
 1               5                  10                  15

Cys Gly Gln Gly Glu Ala Tyr Cys Gly Glu Gly Cys Arg Glu Gly Pro
            20                  25                  30

Cys Asn Lys Pro Ser Pro Thr Pro Gly Gly Ser Ser Leu Ala Glu
        35                  40                  45

Ile Val Thr Pro Asp Phe Phe Asn Gly Ile Ile Asn Gln Ala Ala Ala
    50                  55                  60

Gly Cys Ala Gly Lys Ser Phe Cys Ser Arg Gly Gly Phe Leu Asp Ala
 65                  70                  75                  80

Ala Asn Ser Phe Pro Glu Phe Gly Lys Leu Gly Ser Val Asp Asp Ser
                85                  90                  95

Lys Arg Glu Ile Ala Ala Phe Phe Ala His Val Thr His Glu Thr Gly
            100                 105                 110

His Phe Cys His Ile Glu Glu Ile Asn Gly Ala Ser His Asp Tyr Cys
        115                 120                 125

Asp Glu Gly Asn Thr Gln Tyr Pro Cys Ala Pro Gly Lys Asn Tyr Phe
    130                 135                 140
```

```
Gly Arg Gly Pro Ile Gln Leu Thr Trp Asn Tyr Asn Tyr Gly Ala Ala
145                 150                 155                 160

Gly Asp Ala Leu Arg Leu Asn Leu Leu Gly Ser Pro Glu Met Val Ala
            165                 170                 175

Arg Asp Ala Ala Val Ser Phe Lys Thr Ala Leu Trp Phe Trp Met Lys
        180                 185                 190

Asn Val Arg Pro Val Ile Asn Gln Gly Phe Gly Ala Thr Ile Arg Ala
    195                 200                 205

Ile Asn Gly Ala Ile Glu Cys Asn Gly Gly Asn Pro Gly Thr Val Gln
    210                 215                 220

Ala Arg Ile Gly Tyr Tyr Arg Asp Tyr Cys Ala Lys Phe Gly Val Ala
225                 230                 235                 240

Pro Gly Glu Asn Leu Ser Cys
                245

<210> SEQ ID NO 11
<211> LENGTH: 84
<212> TYPE: DNA
<213> ORGANISM: Carica papaya

<400> SEQUENCE: 11
atgtcgccaa acaatgcctt actcctttct cttcccctcc ttgtttcctt gctcatttcg    60
gccatgccca gaccagtaac gagc                                          84

<210> SEQ ID NO 12
<211> LENGTH: 28
<212> TYPE: PRT
<213> ORGANISM: Carica papaya

<400> SEQUENCE: 12

Met Ser Pro Asn Asn Ala Leu Leu Leu Ser Leu Pro Leu Leu Val Ser
 1               5                  10                  15

Leu Leu Ile Ser Ala Met Pro Arg Pro Val Thr Ser
            20                  25

<210> SEQ ID NO 13
<211> LENGTH: 33
<212> TYPE: DNA
<213> ORGANISM: Carica papaya

<400> SEQUENCE: 13
gtttccttca agacagcctt gtggttttgg atg                                33

<210> SEQ ID NO 14
<211> LENGTH: 11
<212> TYPE: PRT
<213> ORGANISM: Carica papaya

<400> SEQUENCE: 14

Val Ser Phe Lys Thr Ala Leu Trp Phe Trp Met
 1               5                  10

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence:  Synthetic
      6xHis tag

<400> SEQUENCE: 15
```

```
His His His His His His
  1           5
```